United States Patent [19]

Hollister

[11] Patent Number: 5,485,854
[45] Date of Patent: Jan. 23, 1996

[54] SAFETY BLOOD COLLECTION TUBE HOLDER AND ASSEMBLY THEREFOR

[75] Inventor: William H. Hollister, Nelson, N.H.

[73] Assignee: Smiths Industries Medical Systems, Inc., Keene, N.H.

[21] Appl. No.: 226,466

[22] Filed: Apr. 12, 1994

[51] Int. Cl.$^6$ .................................................. A61B 5/00
[52] U.S. Cl. .................................................. 128/763
[58] Field of Search .................................... 128/763–766, 128/770; 604/192, 197, 198, 200, 201

[56] References Cited

U.S. PATENT DOCUMENTS

| | | |
|---|---|---|
| 2,700,973 | 2/1955 | Ju . |
| 3,585,984 | 6/1971 | Buchanan .................................. 128/764 |
| 3,734,080 | 5/1973 | Petterson et al. . |
| 3,886,930 | 6/1975 | Ryan ........................................ 128/764 |
| 4,140,108 | 2/1979 | Nugent . |
| 4,819,659 | 4/1989 | Sitar ........................................ 128/764 |
| 4,840,185 | 6/1989 | Hernandez ............................... 128/763 |
| 4,841,985 | 6/1989 | Wanamaker ............................. 128/763 |
| 5,270,003 | 12/1993 | Bernes et al. ............................ 422/44 |
| 5,279,583 | 1/1994 | Shober, Jr. et al. ..................... 604/198 |

FOREIGN PATENT DOCUMENTS

| | | |
|---|---|---|
| 0337030 | 10/1989 | European Pat. Off. . |
| 0475857 | 3/1992 | European Pat. Off. . |
| 90/04990 | 5/1990 | WIPO . |

*Primary Examiner*—Max Hindenburg
*Attorney, Agent, or Firm*—Pollock, Vande Sande & Priddy

[57] ABSTRACT

A blood collection assembly is disclosed in which the tube holder to which the contaminated end of a blood collection cannula is inserted. To prevent any contaminated blood from being exposed to the user, or bystanders, an elastic pierceable sheath is fixedly aligned within the tube holder so that the tip and at least a portion of the cannula, when fully inserted to the tube holder, are enveloped within the sheath. Any blood dripped from the cannula is therefore retained within the sheath. To obtain samples of blood for testing, a VACUTAINER tube is inserted to the opposite end of the tube holder. The rubber stopper at the top of the VACUTAINER, upon insertion, would slidably push the closed end of the sheath toward the tip of the cannula so that the former is pierced by the latter. Thereafter, the rubber stopper of the VACUTAINER tube is likewise pierced by the cannula so that a fluid communication path is effected between the inside of the VACUTAINER tube and the blood collection bag to which the blood collection cannula is connected. Internal locking means within the tube holder provides fixed retention of the cannula within the sheath and the tube holder so that the cannula would remain in place within the tube holder.

15 Claims, 4 Drawing Sheets

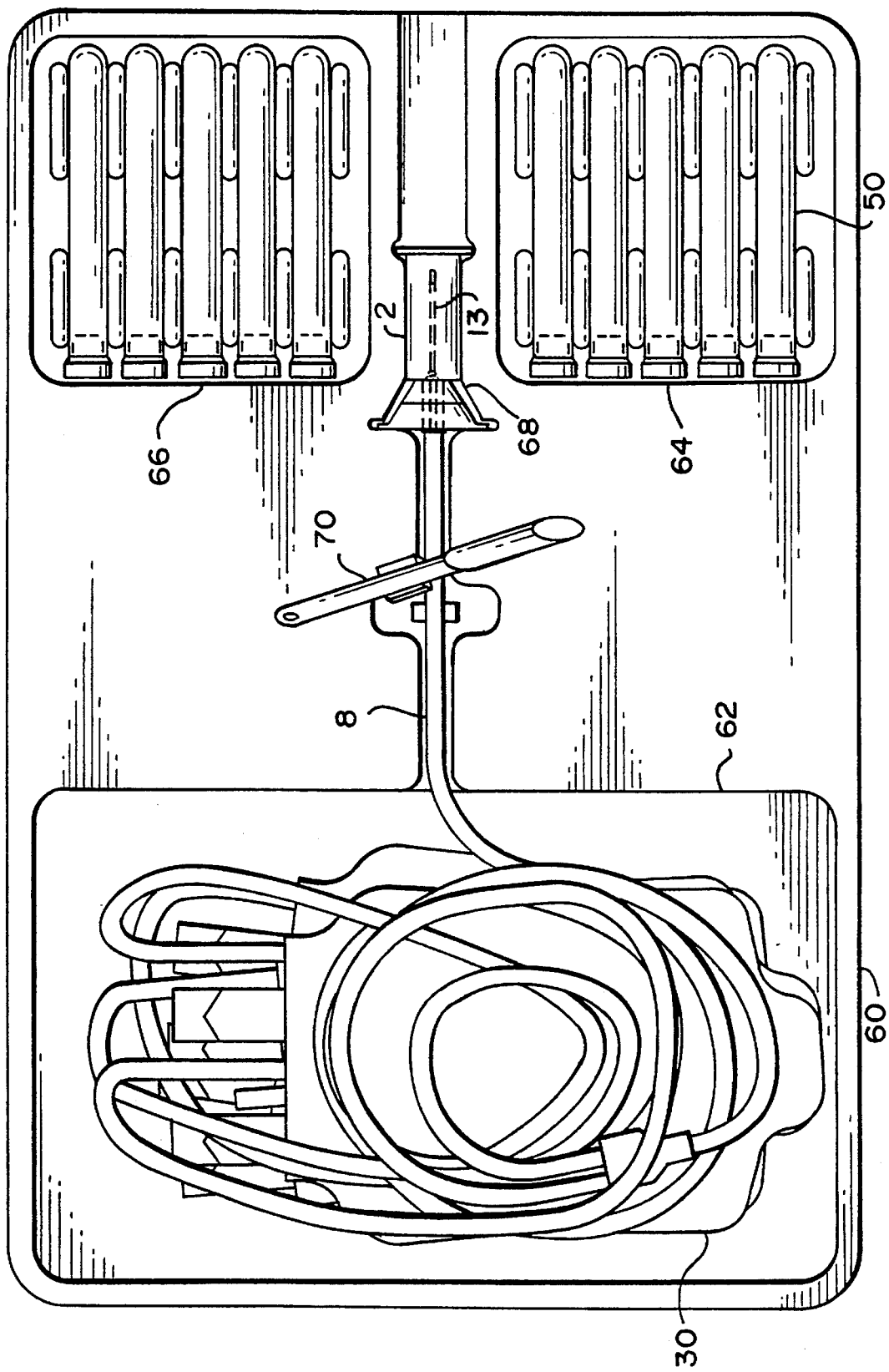

SAFETY BLOOD COLLECTION TUBE HOLDER AND ASSEMBLY THEREFOR

FIELD OF THE INVENTION

This invention relates to blood collection devices and more particularly to a safety tube holder to be used for blood collection. The invention further relates to a tray to be used with the tube holder and its associated blood bags and evacuated blood collection tubes.

BACKGROUND OF THE INVENTION

Blood from a patient is usually withdrawn by means of a blood collection needle and stored in a blood bag. Inside the blood bag is an anticoagulant to ensure that any blood collected will not coagulate. To collect blood, a phlebotomist would insert the needle to the vein of the patient so that blood is drawn and passes via a tube into the blood bag. After the blood bag is filled, the tube is crimped. Different components such as red blood cells, plasma and platelets can be obtained from the blood for further testing or use.

The following problem exists for such conventional blood collection. To wit, once the blood bag is filled, the phlebotomist needs to pull the needle out of the patient's vein. The only thing that the needle is molded to is a piece of elastomer that acts as a hub for the phlebotomist to hold onto. Thereafter, the phlebotomist has to thrust the needle into a blood collection tube, as for example a VACUTAINER tube, so as to remove samples from the blood bag. To do this, the phlebotomist has to hold the VACUTAINER tube in one hand and thrust the needle through a rubber stopper that is fitted to the VACUTAINER tube with her other hand. The vacuum in the VACUTAINER tube causes the blood sample to be drawn, through the needle, from the blood bag. When the VACUTAINER tube is filled, the phlebotomist has to remove the now contaminated needle from the tube. Ordinarily the phlebotomist has to repeat this process a number of time, as a number of VACUTAINER tubes of blood samples are required for the different tests. Accordingly, if a phlebotomist were to take blood from the blood bag for three VACUTAINER tubes, she would have to thrust the needle through three rubber stoppers into three different VACUTAINER tubes. Thus, there are three chances that she could miss the rubber stopper and instead have the needle (contaminated after the first use) stab her hand at the area between her thumb and wrist. Needless to say, with the current crop of blood-borne contagious diseases, such inadvertent exposure to contaminated blood needs to be prevented.

There is a product in the market which allows a phlebotomist to snap a needle thereinto, for piercing the rubber stopper of a VACUTAINER tube. However, this available product does not protect a user from contaminated blood that may be dripping from the end of the needle.

SUMMARY OF THE PRESENT INVENTION

To ensure that no contaminated blood is exposed to the environment, the present invention tube holder has fitted thereinto an elastomeric tubular sheath having one open end and a closed yet pierceable end. The sheath is in alignment along the longitudinal axis of the tube holder, with its open end positioned toward the end of the tube holder to which the needle (cannula) is to be inserted. To protect the user's hand, especially at the area between the thumb and wrist, an integral protective shield large enough to protect the just mentioned area of the user's hand extends from the needle insertion end of the tube holder. There is also an internal circular flange within the tube holder to which the elastic tubular sheath is anchored, for example by means of a grommet. Extending toward the end of the protective shield are elastic clips for locking the needle, more precisely the hub of the needle, in place once the needle has been inserted to the tube holder and at least the tip portion of the cannula is enveloped by the tubular sheath.

Thus, once a phlebotomist has withdrawn the blood collecting needle from the vein of a patient (after the appropriate units of blood have been drawn into the blood bag to which the cannula is attached per tubing), instead of just holding the now blood soaked cannula and thereby exposing the same to the environment, the phlebotomist would insert the cannula to the end of the tube holder which has the protective shield, which protects the other hand of the phlebotomist as the cannula is being inserted to the tube holder. Upon the proper insertion, the cannula becomes fixedly retained within the tube holder and enveloped by the elastic sheath. Accordingly, any contaminated blood that may be dripping from the cannula is contained within the sheath.

To obtain blood samples from the blood bag, a VACUTAINER tube is inserted to the other end of the tube holder. Inasmuch as the VACUTAINER tube is sealed by an elastomer, for example a rubber stopper, when the VACUTAINER tube is inserted to the tube holder, the rubber stopper would slidably push against the sheath enveloping the cannula such that eventually first the sheath, and then the rubber stopper, are pierced by the tip of the cannula to effect a fluid communication path between the VACUTAINER tube and the blood bag. Due to the vacuum in the VACUTAINER tube, blood is drawn thereinto. The VACUTAINER tube is withdrawn from the tube holder once it is full. Upon withdrawal of the VACUTAINER tube from the tube holder, the elastic sheath returns to its original configuration to thereby again envelop the cannula. Additional samples of the blood for testing may be obtained by inserting additional VACUTAINER tubes to the tube holder.

An objective of the present invention is therefore to provide a tube holder that can protect the hand of a user when a blood collecting needle is to be inserted thereto.

It is another objective of the present invention to provide a tube holder that can act as a valve for preventing the accidental exposure of contaminated blood to the user, or anyone else.

BRIEF DESCRIPTION OF THE DRAWINGS

The above-mentioned objectives and advantages of the present invention will become more apparent and the invention will best be understood by reference to the following description of embodiments of the present invention taken in conjunction with the accompanying drawings, wherein:

FIG. 4 is a plan view of a tray showing the different compartments therein for storing the various components of a blood collecting assembly.

DETAILED DESCRIPTION OF THE INVENTION

Figure 1:
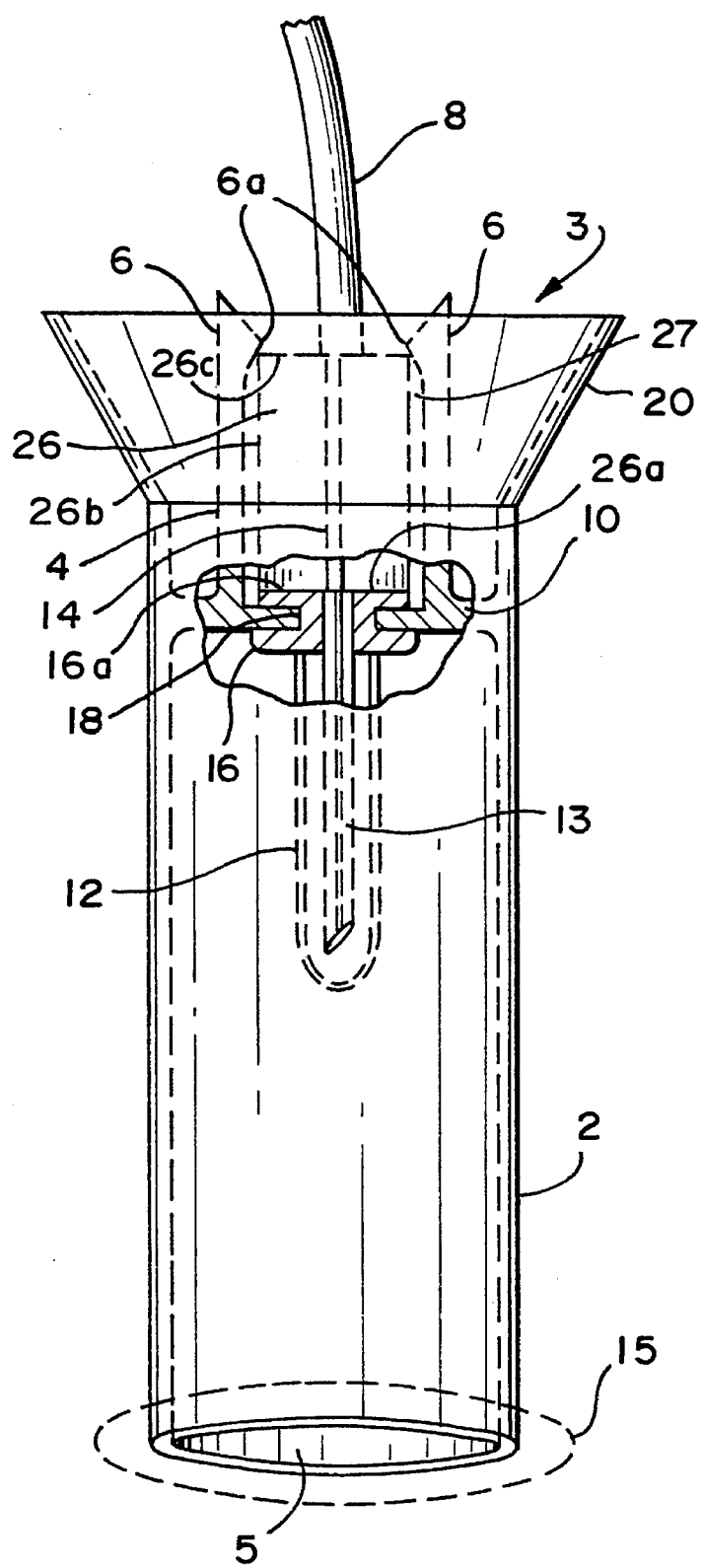
FIG. 1 is a semi-exposed side view of the tube holder of the instant invention.

With reference to FIG. 1, the tube holder of the present invention is shown to comprise a plastic barrel main body portion 2 that has a first open end (opening) 3 and a second open end 5. A flared lip extends circumferentially from the end of tube holder 2 at opening 3 to form a protective shield 20, or an escutcheon shield when viewed from FIG. 2B about the opening at open end 3. Protective shield 20 is of sufficient dimension to coveredly protect the portion of a user's hand extending from her thumb to forefinger and wrist.

Away from open end 3 within tube holder 2 is an internal circumferential flange 10 for accepting a grommet 16 to which an elastomeric tubular sheath 12 is molded. For the embodiment shown in FIG. 1, extending from the upper part of flange 10 are at least two semi-rigid snap extensions 6.

As further shown in FIG. 1, a blood collection needle, as exemplified by cannula 13, is shown to be connected to a conduit, or tube 8, which in turn is connected to and extends from a blood bag 30, shown in FIG. 4. Molded around the upper portion of cannula 13 is a housing or hub 26 having a key 14 extending longitudinally therealong. The horizontal dimension of hub 14 is such that it is somewhat larger than the distance separating the two tips 6a of snap extensions 6. Accordingly, when cannula 13 is inserted to opening 3, as hub 26 is guided along tube holder 2 by key 14 through a slot 15 (shown in FIG. 2A), hub 26 would force snap extensions 6 slightly apart, as its sides make contact with tips 6a of snap extensions 6. When fully inserted, as for example when bottom surface 26a of hub 26 makes contact with top surface 16a of grommet 16, hub 26 is fully positioned within space 27 defined by snap extensions 6. Once the top portion of hub 26, particularly top surface 26c, passes tips 6a, snap extensions 6 would return to their original position to thereby fixedly retain hub 26 within space 27. Of course, inasmuch as cannula 13 is molded to hub 26, and since it has passed through grommet 16 into elastomer sheath 12 as hub 26 is fixedly retained by extensions 6, it is completely enveloped by sheath 12. Thus, any contaminated blood that would have dripped from cannula 13 is collected within sheath 12, as sheath 12 acts as a septum for preventing any fluid from passing therethrough.

To enable tube holder 2 to stand upright so that a user does not necessarily has to hold onto it, an optional circumferential flange 15 (shown in dotted line) extending from the edge of opening 5, may be integrated to tube holder 2.

Figure 2A:
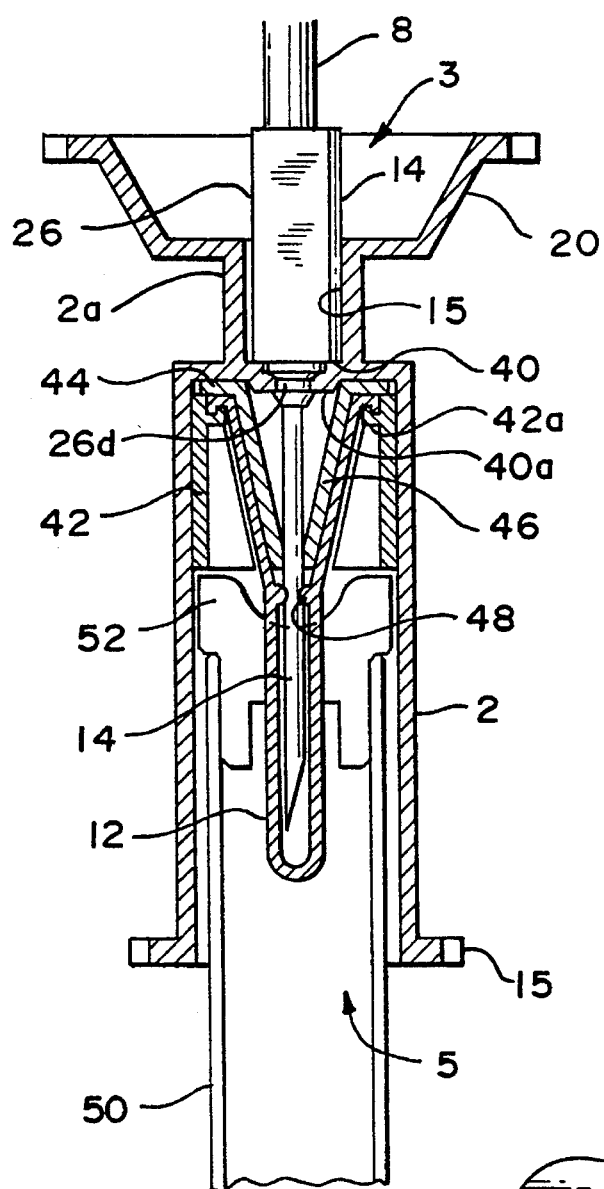
FIG. 2A is an exposed side view of a second embodiment of the instant invention.
Figure 2B:
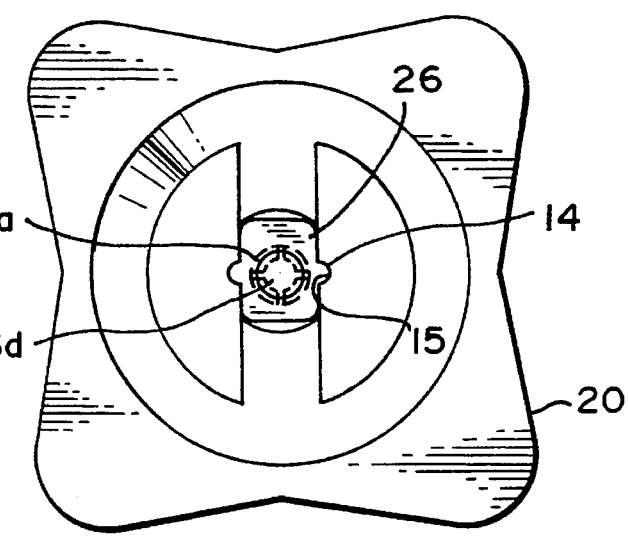
FIG. 2B is a plan view of the tube holder, and more particularly the protective shield, of the FIG. 2A embodiment of the present invention.

FIGS. 2A–2B illustrate a second embodiment of the instant invention. Parts which function similarly or are the same as those described in FIG. 1 are labelled the same.

With reference to FIG. 2A, tube holder 2 now is shown to have an added portion 2a extending from the main tube portion of tube holder 2. Integrated to extension 2a is the escutcheon protective shield 20. Instead of internal flange 10 per the FIG. 1 embodiment, an internal circumferential lip 40 is provided between the intersection of the main tube portion and extension 2a of tube holder 2. Instead of snap extensions 6 as shown in the FIG. 1 embodiment, lip 40 has extending fingers 40a, which act to secure hub 26 of cannula 13 to tube holder 2. As should be readily apparent, the configuration of hub 26 is such that a groove 26d is provided at essentially the lowermost portion thereof to interact with fingers 40a for fixedly retaining hub 26, and therefore cannula 14, in place, after the needle assembly has been inserted to tube holder 2.

Further shown in FIG. 2A is an elastic tubular sheath 12, which is somewhat different from that of the FIG. 1 embodiment. Specifically, sheath 12, for the FIG. 2 embodiment, is held in place by means of a circumferential hanger 42 welded to the upper interior portion of tube holder 2. The top portion of sheath 12 has a circular hanging lip 44, which mates with the support fingers 42a of holder 42. To further secure sheath 12 within tube holder 2, and to further prevent the tip of cannula 14 from piercing the upper sides of sheath 12, a plastic insert 46 is pressedly fixed to the upper portion of sheath 12.

In operation, for the FIG. 2A embodiment, as cannula 14 is inserted to opening 3 and later through the opening of flange 40, key 14 of hub 26 is guided within slot 15 to thereby effect a smooth and steady insertion of cannula 14 to sheath 12. As shown, the tip of cannula 14, as well as a major portion thereof, is contained within sheath 12. A circumferential nub 48 internal to sheath 12 further provides the snug guidance for cannula 14, as it is being inserted to sheath 12.

As was the case with the FIG. 1 embodiment, once cannula 14 is properly inserted to tube holder 2, it is fixedly retained thereto, by means of the interaction between finger 40a of flange 40 of tube holder 2 and groove 26d of hub 26. Thus, when a VACUTAINER tube 50 is inserted to opening 5 of tube holder 2, its elastomer sealer or rubber stopper 52, even though pushing up against the tip of cannula 14, would not dislodge the same from its location within tube holder 2. More precisely, as VACUTAINER tube 50 is being inserted, the top portion of stopper 52 would push against the closed portion of sheath 12. As the VACUTAINER is further pushed inwards within tube holder 2, sheath 12 is slidably pushed backwards until it is pierced by the tip of cannula 14. Thereafter, the tip of cannula 14 further pierces stopper 52 so that eventually it effects a fluid communication path between the inside of VACUTAINER tube 50 and tube 8. Once VACUTAINER tube 50 is withdrawn from tube holder 2, sheath 12 would return to its original state so that any blood that may have dripped from cannula 14 would remain inside sheath 12.

FIG. 2B is a plan view of the FIG. 2A embodiment and shows shield 20 and the mating of hub 26 within extension 2a of tube holder. In particular, as shown, key 14 of hub 26 is being guided within slot 15 formed within extension 2a of tube holder 2. Groove 26d is also shown, as are fingers 40a of flange 40.

Figure 3:
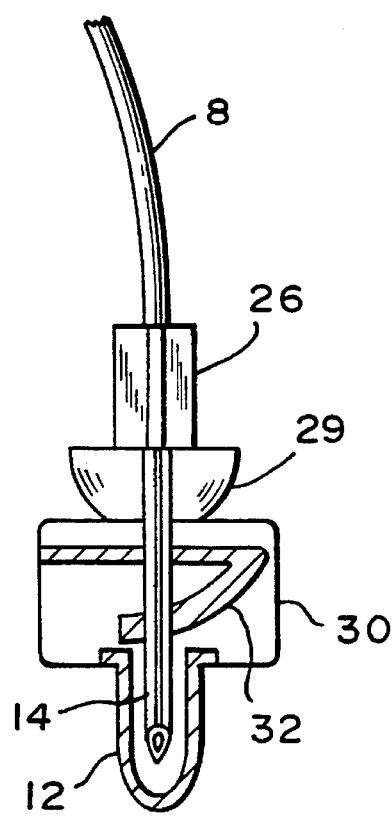
FIG. 3 is a side view of the present invention showing another locking mechanism for retaining a blood collecting needle in place.

FIG. 3 shows a modification to the embodiments of FIGS. 1 and 2. In particular, it shows the retention of cannula 14 within sheath 12 by means of a semi-rigid friction ring 32 that is V-shaped. Portion 30 is formed within tube holder 2, with a cup 29 for receiving hub 26. For the FIG. 3 embodiment, cannula 14 itself is shown to be fixedly retained within sheath 12. This retention can be by itself, or it can be used in conjunction with either the snap extensions 6 of the FIG. 1 embodiment or the groove/fingers interaction of the FIG. 2 embodiment.

FIG. 4 is a plan view of a tray 60 used in conjunction with tube holder 2. As shown, tray 60 has a first compartment 62 for storing a plurality of blood bags 30. Further shown in tray 60 are additional compartments 64 and 66, each for storing a plurality of VACUTAINER tubes 50. Fitted to the center portion of tray 60, at an appropriate chamber 68, is tube holder 2. Further shown pivotally coupled to tray 60 is a cutter adaptable to cut tube 8 and heat seal the same. To achieve sealing of tube 8, power is applied to cutter 70, either by AC power or a battery (not shown). Thus, once the necessary samples are withdrawn from blood bag 30, a user would cut tube 8 and apply heat at the cut end to seal the same. Of course, the now used tube holder 2 with the contaminated cannula 13 fixedly retained therein can be disposed of. Any additional blood to be taken from blood bag 30 can be done by reopening the heat sealed tube and inserting a new cannula thereto.

Figure 5:
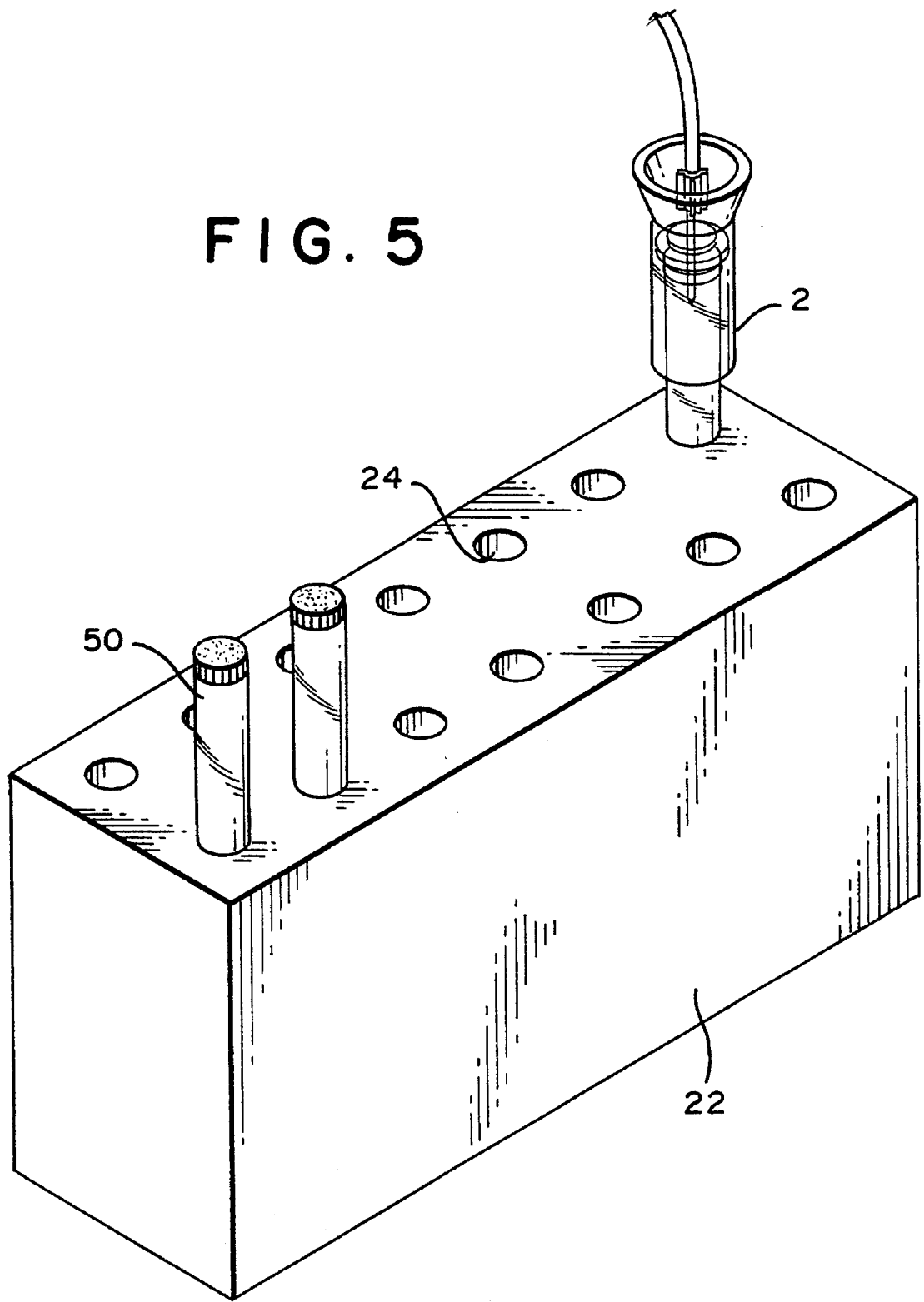
FIG. 5 shows a storage rack into which a plurality of VACUTAINER tubes may be stored for interaction with the tube holder of the present invention.

FIG. 5 is an illustration of a retainer block 22 in which a number of VACUTAINER tubes 50 may be inserted to the respective holes 24. Block 22 thereby enables a user to quickly mate cannula 14 to a number of VACUTAINER tubes by pushing tube holder 2 over those tubes. This easily enables a user to obtain the appropriate number of samples of blood.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only be the spirit and scope of the hereto appended claims.

I claim:

1. A blood collection safety apparatus comprising:

a tube holder having a first and second end for accepting a cannula of a blood collecting device and blood collection robes each sealed with an elastomer, respectively, said first end of said tube holder having a protective shield extending therearound;

an elastic tubular sheath fixedly retained and aligned within said tube holder, said sheath having an open end and a closed pierceable end fixedly located relative to said first and second end of said robe, respectively;

wherein when a cannula is inserted to said first end of said tube holder, at least the tip of said cannula passes through said open end of said sheath so as to be enveloped by said sheath; and wherein when a blood collection robe is inserted to said second end of said tube holder, said elastomer of said collection tube slidably pushes back said closed end of said sheath so that said closed end and said elastomer are pierced by the tip of said cannula and a fluid communication path is effected from said blood collection tube to said cannula.

2. Apparatus of claim 1, further comprising:

locking means within said tube holder for fixedly retaining a hub fitted about a cannula to thereby maintain said cannula within said tube holder after said cannula is inserted through said first end.

3. Apparatus of claim 1, further comprising:

flange extending about said second end of said tube holder to enable said tube holder to stand upright on its second end.

4. Apparatus of claim 1, wherein said elastic tubular sheath is fixedly retained within said tube holder by an elastomeric grommet mated with a ring extending inwardly within said tube holder.

5. Apparatus of claim 1, further comprising:

an elastomeric friction locking means fitted within said tube holder for fixedly retaining a cannula once said cannula is inserted to said tube holder.

6. Apparatus of claim 1, wherein when a cannula having a hub including a key extending longitudinally therealong is inserted to said tube holder, said hub is guided by said key matingly fitted to a slot along an internal flange of said tube holder through which said cannula passes.

7. Apparatus of claim 1, wherein said protective shield is sufficiently large for protecting the hand and fingers of a user holding said tube holder.

8. Apparatus of claim 1, wherein said blood collecting device comprises a blood bag having an elastic tube extending therefrom and to whose opening a cannula is mated.

9. A tube holder comprising:

a tubular member having a first end with a circumferential shield extending therefrom for accepting a cannula of a fluid collecting device and a second end for accepting fluid collection tubes;

an elastic tubular sheath fixedly retained and aligned within said tubular member for accepting at least the tip of a cannula, said sheath having an open end through which said tip of said cannula passes and a closed pierceable end for preventing any fluid dripping from said tip from escaping.

10. The tube holder of claim 9, further comprising:

locking means integral internally proximate to said first end of said tubular member for fixedly retaining a hub of a cannula to thereby maintain said cannula within said tubular member after said cannula has been inserted through said first end.

11. The tube holder of claim 9, further comprising:

flange extending about said second end of said tubular member for enabling said tube to stand upright on its second end.

12. The tube holder of claim 9, wherein said elastic tubular sheath is fixedly retained within said tubular member by an elastomeric grommet mated with a circumferential flange extending inwardly within said tube holder.

13. The tube holder of claim 9, further comprising:

an elastomeric friction locking means fitted within said tubular member for fixedly retaining a cannula once said cannula is inserted to said tube.

14. The tube holder of claim 9, further comprising:

a slot cut along an internal flange of said tubular member for mating with a key extending longitudinally along a hub of a cannula inserted to said tubular member so that said hub is guided longitudinally by said slot.

15. The tube holder of claim 9, wherein said protective shield is sufficiently large for protecting the hand and fingers of a user holding said tube holder.

* * * * *

UNITED STATES PATENT AND TRADEMARK OFFICE
CERTIFICATE OF CORRECTION

PATENT NO. : 5,485,854
DATED : January 23, 1996
INVENTOR(S) : William H. Hollister It is certified that error appears in the above-indentified patent and that said Letters Patent is hereby corrected as shown below:

Column 5, line 31, change "robes" to --tubes--.

Column 5, line 37, change "robe" to --tube--.

Column 5, line 42, change "robe" to --tube--.

Signed and Sealed this

Second Day of April, 1996

Attest:

BRUCE LEHMAN

Attesting Officer

Commissioner of Patents and Trademarks